United States Patent [19]

Gram

[11] 4,290,343
[45] Sep. 22, 1981

[54] HIGH VOLUME POPPET VALVE WITH ORIFICE OPENING SPEED CONTROL

[75] Inventor: Martin M. Gram, Minneapolis, Minn.

[73] Assignee: MTS Systems Corporation, Eden Prairie, Minn.

[21] Appl. No.: 955,964

[22] Filed: Oct. 30, 1978

[51] Int. Cl.³ ............... F15B 13/042; F16K 31/122
[52] U.S. Cl. ...................................... 91/461; 73/837;
91/5; 251/25; 251/48
[58] Field of Search ............... 91/461; 92/134, 60;
251/25, 47, 48; 73/837

[56] References Cited

U.S. PATENT DOCUMENTS

| | | | |
|---|---|---|---|
| 2,587,539 | 2/1952 | Seaman | 251/25 X |
| 2,815,008 | 12/1957 | Hirt | 92/134 X |
| 2,911,005 | 11/1959 | Adelson | 91/454 |
| 3,282,283 | 11/1966 | Takeda | 91/461 X |
| 3,434,393 | 3/1969 | Cairatti | 91/461 X |
| 3,980,002 | 9/1976 | Jarman et al. | 91/461 |
| 4,007,667 | 2/1977 | Elias et al. | 92/60 |
| 4,093,002 | 6/1978 | Tardy | 91/445 X |

FOREIGN PATENT DOCUMENTS

| | | | |
|---|---|---|---|
| 1807788 | 11/1968 | Fed. Rep. of Germany | 92/134 |
| 244469 | 4/1926 | United Kingdom . | |
| 1538128 | 1/1979 | United Kingdom . | |

*Primary Examiner*—Irwin C. Cohen
*Attorney, Agent, or Firm*—Kinney, Lange, Braddock, Westman and Fairbairn

[57] ABSTRACT

A high volume valve for controlling flow of fluid from a source of fluid under pressure, such as in an accumulator, to an actuator used for testing specimens under high rates of loading. The valve includes a poppet type valve piston that is normally held in a closed position by hydraulic pressure behind the poppet, and when the pressure holding the poppet closed is released, the main supply of fluid under pressure acts on the poppet to open it very quickly. A second accumulator open to the opposite side of the poppet from the main source of pressure is utilized for controlling speed of opening of the valve. The amount the poppet opens also can be adjusted for controlling the rate of flow of fluid from the main source of pressure to the actuator.

8 Claims, 2 Drawing Figures

HIGH VOLUME POPPET VALVE WITH ORIFICE OPENING SPEED CONTROL

CROSS REFERENCE TO RELATED APPLICATION

This invention describes certain improvements over my copending application Ser. No. 955,807, filed on even date herewith for RAPID OPENING, HIGH FLOW CONTROL VALVE FOR HYDRAULIC ACTUATOR.

BACKGROUND OF THE INVENTION

1. Field of the Invention

The present invention relates to a high volume valve that permits a high flow of an actuator in a short period of time.

2. Prior Art

In the past, MTS Systems Corporation of Eden Prairie, Minn., has built what is known as a velocity generator. This is an actuator that provides a relatively high rate of movement. These actuators generally are directly coupled to a pressure source, and have an internal inlet port controlled by a seal on the actuator piston of the velocity generator. The piston is held in position closing the port and when triggered the force holding the piston is reduced and the piston moves slightly and then the entire piston is open to the supply pressure from the built-in accumulator surrounding the velocity generator actuator. Such velocity generators are used for dynamic test systems for impact testing of automotive interiors for example.

Additionally, in the prior art when high velocity actuators were to be used for testing specimens, it has been known to control such actuators with large solenoid valves that will handle up to 400 gallons per minute. Such valves are large, expensive and do not open as quickly as desirable.

SUMMARY OF THE INVENTION

A high rate volume valve that utilizes a poppet type valve piston normally held closed by fluid pressure and which would when fired open rapidly to permit fluid pressure from a source to be provided to an actuator in a short period of time. The opening movement of the poppet is cushioned and controlled through the use of an accumulator acting through an orifice so that as the poppet valve opens the orifice and the accumulator control the speed of opening. Means are also provided as shown to control the stroke of opening of the poppet to control the ultimate velocity or rate of transfer of fluid under pressure from the main source to the actuator.

DESCRIPTION OF THE PREFERRED EMBODIMENT

Figure 1:
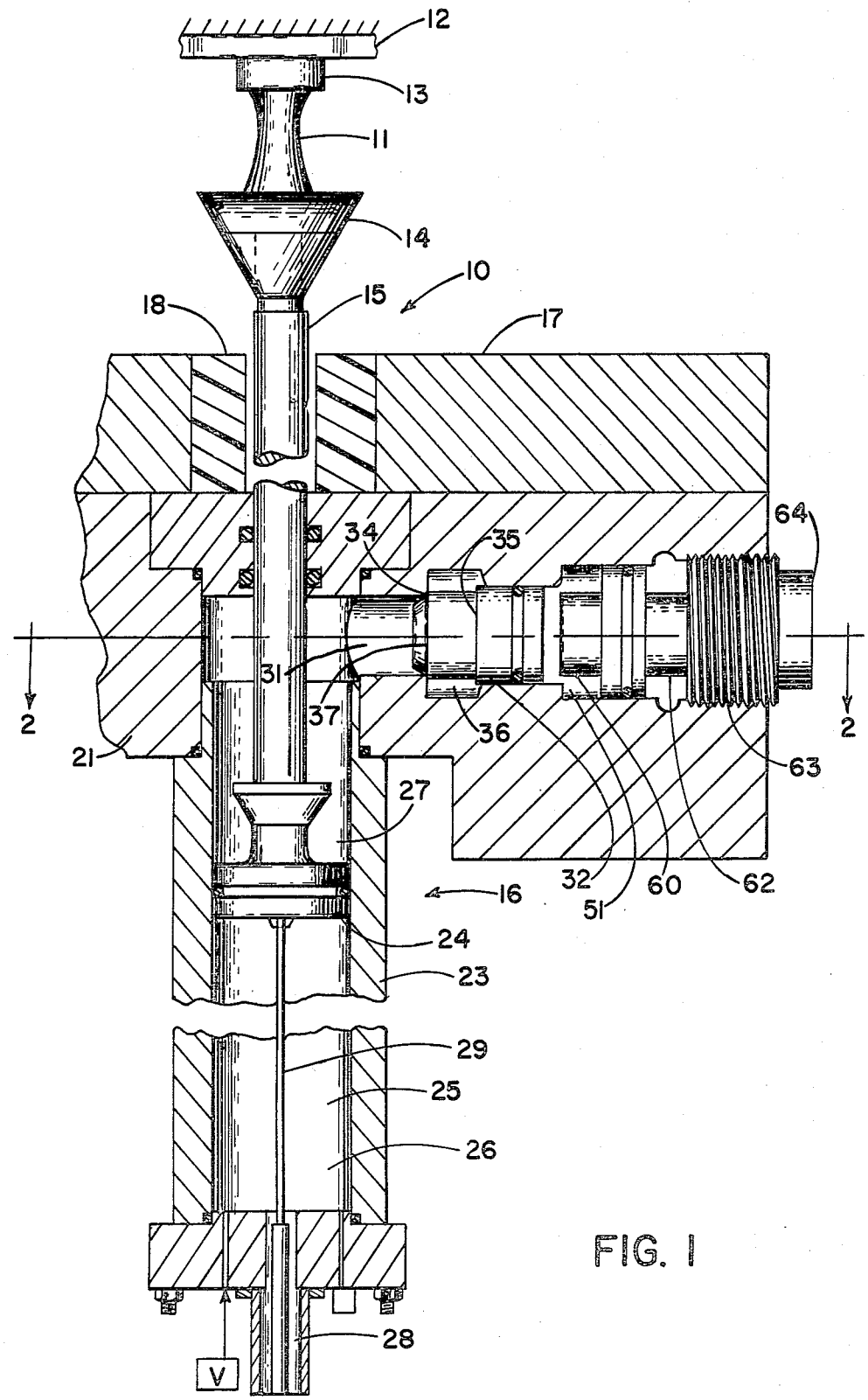
FIG. 1 is a fragmentary part schematic vertical sectional view of an actuator utilized with the high rate opening valve of the present invention.

An actuator assembly illustrated generally at 10 in the drawings is used for tensile testing of specimens, such as a specimen 11. The assembly includes a load frame crosshead represented schematically at 12, and upper specimen grip 13, which can also include a load cell for sensing the load in the specimen on the crosshead. The upper grip 13 holds the upper end of the specimen 11. A lower grip 14 is provided for holding the lower end of the specimen 11, and this lower grip 14 in turn is connected to the output shaft 15 of an actuator assembly 16. The actuator assembly 16 is mounted to a load frame base plate shown schematically and fragmentarily at 17 of usual design, through suitable connectors, and as shown includes a hard rubber block 18 that will absorb some loads. A manifold assembly 21 is mounted below the base plate 17, and can be held against the base plate in any suitable manner such as through the use of cap screws or the like.

The actuator assembly 16, in addition to having an output rod 15, has a cylinder member 23, in which an internal piston 24 is mounted in the normal manner, and the piston 24 is attached to the rod 15. The piston 24 divides the interior chamber 25 of the cylinder 23 into two separated chambers, including a lower cushion chamber 26 and an upper actuating chamber 27. A suitable displacement transducer 28 is connected to the base plate of the cylinder 23 and also has a sensing rod 29 that is connected to the piston 24 in the normal manner.

The manifold, as shown, receives the open upper end of the cylinder 23, and thus the chamber 27 is open through a suitable port or passageway 31 in manifold 21 to a first end surface of a poppet valve or valve piston 32. The valve piston is mounted in a bore indicated at 33 in the manifold 21, and this bore 33 is of slightly larger diameter than the passageway 31. The junction of the two passageways forms a shoulder 34 in the manifold that comprises a valve seat facing away from the actuator chamber 27 and surrounding the passageway 31.

The valve piston 32 comprises a poppet type valve that is slidably mounted in the bore 33, and has a suitable "O" ring for pressure sealing. The valve piston 32 as shown has a turned down end that seats on shoulder 34 and the turned down end forms an intermediate shoulder 35. The valve piston 32 has a second shoulder 37 which mates with and seats against the shoulder 34 to form a seal or seat for seating of the valve piston.

An annular recess 36 surrounds the bore 33 and the valve piston 32 at an intermediate portion between shoulders 35 and 37. The recess 36 is open through an inlet passageway 40 to a first chamber 41 of an accumulator assembly formed directly in the manifold and comprising a movable piston 42 that is slidably mounted in the chamber 41 and which piston is retained in position with an internal collar 43 threadably mounted in place. A second accumulator chamber 44 is formed on an opposite side of the piston 42 from the passageway 40, and chamber 44 is filled with a suitable gaseous fluid under suitable pressure. The chamber 44 is closed with an end block 45. The pressure in chamber 44 will tend to move the piston 42 toward the passageway 40 to reduce the volume of chamber 41. Chamber 41 is filled with a hydraulic oil which is provided through the valve opening and through passageway 31 to actuate the actuator assembly 16, as will be explained. The end block 45 includes a suitable passageway leading to a valve 46 that can be utilized for filling the chamber 44 with a desired fluid under the desired pressure from a source.

Likewise, a valve 50 (see FIG. 2) is provided for filling the chamber 41 and passageway 40 with a suitable hydraulic fluid from a pressure source. Valve 50 is a solenoid valve which also can be used for connecting this chamber 41 to "return" or drain if desired.

The bore 33 leads to a chamber 51 that opens to the opposite end of the valve body 32 from the shoulder 37, and this chamber 51 is charged with a suitable amount of hydraulic fluid through a normally open valve 52 leading from a pressure source. The pressure from the source is normally applied to chamber 51. The chamber 51 also is open through an orifice 53 to an accumulator assembly indicated generally at 54 formed in the manifold 21. The accumulator assembly 54 includes an internal piston 55 which has one face open to the orifice 53, as shown, and the opposite side of the piston is open to a chamber 56 that is charged with a suitable amount of gaseous fluid under pressure through a control valve 57 and suitable passageways. The piston 55 is sealingly slidable relative to the chamber in which it is mounted and exerts a relatively low pressure, for example, 400 psi.

Figure 2:
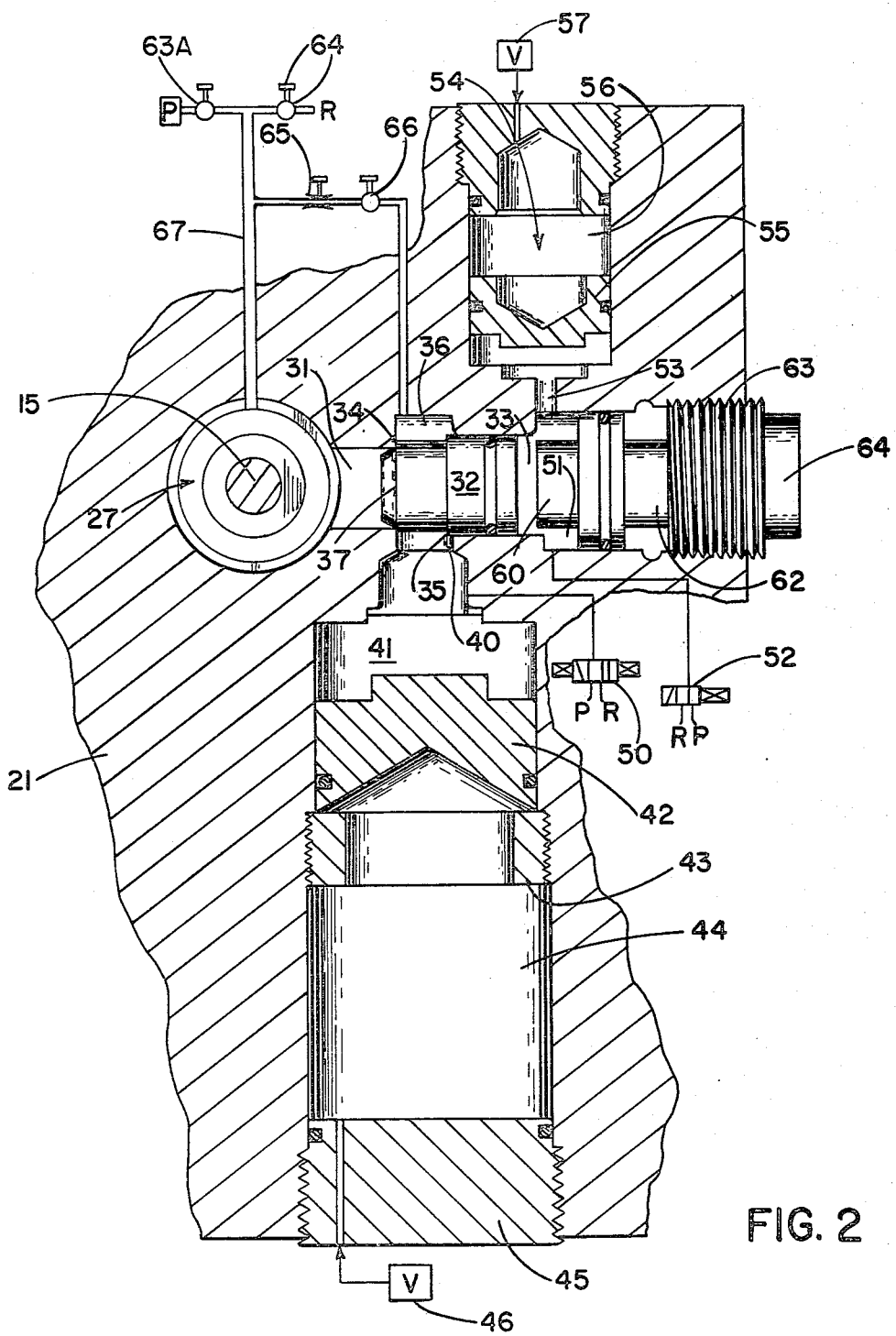
FIG. 2 is a fragmentary sectional view taken generally on line 2—2 in FIG. 1.

The chamber 51 also houses an adjustable stop bumper 60 that is mounted onto the end of a sealing spool or plug 62 which can be controlled through a micrometer thread adjustment indicated generally at 63 using a hand control knob 64. The spool has a portion which seals one end of the chamber 51. By turning the knob 64 and the adjusting member 63 in suitable threads formed in the manifold, the position of the end of the stop block 60, which faces poppet or valve piston 32 can be changed so that the spacing between the end of the valve piston 32 in its closed position (as shown in FIG. 2) and the end of this block 60 can also be changed.

Note that the valve piston 32 has an "O" ring on a second end portion for sealing in the bore 33 to seal chamber from the pressure inlet recess 36.

In running tests on specimen 11, the position of the actuator piston 24 can be controlled by operating a suitable manual valve 63A that leads from a pressure source to the chamber 27 through a conduit 67, or by operating a second manual valve 64 which leads from the chamber 27 through the conduit 67 to a return or drain. A hand valve 66 and a needle valve 65 may be provided in a conduit 67A that leads from the recess 36, and thus from the chamber 41 to the conduit 67, which is connected to the chamber 27. The purpose of the needle valve 65 is to permit manual control of the loading of the specimen for conducting tests at lower rates. Thus, manual control of the test can be achieved. The poppet or valve piston 32 would remain closed during manual operation.

The valve 66 is normally closed and needle valve 65 is not used. The valves 63A and 64 are used only to adjust the grips and specimen 11 to the desired relationship. At that time both the valves 63A and 64 are closed, so that the chamber 27 operates like any other closed chamber in a hydraulic actuator. It is filled with hydraulic oil but not under pressure, unless preload of the specimen is desired.

With the unit set as shown in FIGS. 1 and 2, that is, with the valve piston 32 in a closed position and held there by pressure in the bore 33 and control chamber 51 for the valve piston, as controlled by the pressure source connected to valve 52, it is first made sure that the chamber 26 is filled with a suitable amount of gaseous fluid under pressure such as nitrogen, to provide a cushion for the piston 24 when the specimen fractures. Then the valve 52 is operated to dump the pressure in the control chamber 51 to drain or reservoir. As soon as the pressure in the chamber 51 drops, the pressure in the chamber 41 acting through passageway 40 will act on the shoulder 35 of the valve piston 32 forcing it to the right as shown in FIG. 2, toward the block 60. As soon as the shoulder 37 separates slightly from the valve seat shoulder 34 in the manifold, the full pressure of the accumulator assembly formed by piston 42 will act on the poppet or valve piston 32 forcing it toward the block 60. At the same time the hydraulic oil in the chamber 51 will be forced through the orifice 53 against the piston 55 which is cushioned by a gas such as nitrogen, for example, in the range of 400 psi. The valve piston 32 then will open at a fast but controlled rate as determined by orifice 53, which is substantially larger in cross sectional size than the size of the openings in the valve 52. The effect of valve 52 on the rate of opening of valve piston 32 is negligible. The piston 55 will compress the gas in chamber 56. The passageway 37 will be fully open to the passageway 40 resulting in a fast flow or in-rush of hydraulic oil into the chamber 27 forcing the piston 24 downwardly and testing the specimen at the desired load and speed depending on the pressure in the accumulator chamber 44, the volume of hydraulic oil in chamber 41, and the amount that valve piston or poppet 32 is permitted to open. The piston 42 may bottom adjacent passageway 40 so that the volume of hydraulic oil that is used for operating the actuator can be controlled to a set volume.

It should be noted that the action of the accumulator piston 55 used for cushioning movement of valve 32 not only controls the speed of opening of the valve and the size of the orifice 53, but also reduces the acceleration transients on the actuator. By limiting the speed of the valve piston or poppet 32 the block 60 does not have to be a special cushion or stop member. Further, the stroke of the valve piston 32 is controlled by the adjustment of the threaded member 63 so that the amount the valve piston opens can be controlled directly to control the flow from the chamber 41 without the need for a second flow control valve.

Usually for high testing rates, in the range of one hundred to one thousand inches per second, the piston 24 requires some distance of travel before it reaches its maximum speed, and thus the grips 13 and 14 can be slack grips that permit some movement of the piston prior to the time that the specimen is pulled so that the specimen is not pulled until the actuator has reached its desired speed. In medium rate testing, for example, in the range of ten to three hundred inches per second, the specimen 11 would be attached without slack in the grips, and the acceleration distance can be between 0.0001 and 0.1 inches of movement.

The needle valve 65 and valve 66 can be used for a quasi-static type testing to have very low rates of acceleration in the region of one tenth to ten inches per second, and this is done by providing a manually controlled path for flow through the needle valve 65, after opening the valve 66 from chamber 41. Suitable controls can be used for charging the accumulators, and the fire valve 52, which is a solenoid valve, can have a remote actuation so that the operator does not have to be nearby when the test is actually being carried out. The manifold 21 has integral porting and passageways such as 37 leading to the chamber 27 to provide for high flow rates. The fast acting poppet valve will open in the range of one millisecond.

The pressure in the main accumulator will normally be in the range of 2500 psi, substantially greater than the pressure on piston 55.

If desired, the cushion for the actuator piston can be an accumulator open to lower chamber 26, which would be filled with hydraulic oil. The rate of escape of the oil from chamber 26 could be controlled to provide the necessary cushion.

What is claimed is:

1. In combination with a first source of fluid under pressure and a hydraulic motor, the improvement comprising a control valve having a valve body having an inlet port coupled to the first source of fluid under pressure and an outlet port coupled to the hydraulic motor, a bore in said valve body, a poppet valve member mounted in said bore, means forming a valve seat surrounding said bore, said poppet valve member having a first portion engaging said seat to seal off flow from said inlet port to said outlet port when the poppet valve member is in a closed position, and said poppet valve member having a second portion of minimal cross sectional area open to the inlet port when the poppet valve is in closed position, means forming a control chamber on an opposite end of said poppet valve member from said valve seat, an accumulator providing a second fluid pressure separate from said first source of fluid under pressure to said control chamber to hold said poppet valve member against said seat, valve means having a valve opening operable to release the fluid pressure in said control chamber to permit said poppet valve member to move away from the seat, pressure at the inlet port thereafter acting to move the poppet valve member away from said seat across substantially the entire cross sectional area of the poppet valve member, said poppet valve member being moved to an open position to permit said inlet port to communicate with the outlet port across said valve seat, means other than the valve means to release forming an orifice substantially larger than the opening of the valve means to release leading from the control chamber to said accumulator to control the flow of fluid from said control chamber, and to regulate the speed of the poppet valve member as it is opened after it has moved away from said seat.

2. The combination as specified in claim 1, and threadable adjustable means mounted in said valve body and being threadable toward and away from the end of said poppet valve member opposite from said seat to limit the amount that said poppet valve member can move away from said seat.

3. The control valve of claim 1 wherein said second fluid pressure in said control chamber comprises hydraulic oil under pressure.

4. A control valve comprising a valve body having an inlet port connected to a first source of substantially incompressible fluid under pressure and an outlet port adapted to be connected to a hydraulic motor, a bore in said valve body between said inlet port and outlet port, a poppet valve member slidably mounted in said bore and comprising a poppet piston having a first end portion, an intermediate portion and a second end portion, shoulder means forming a valve seat surrounding said bore, said poppet valve member having a surface adjacent the first end portion thereof engaging said valve seat to seal off flow from said inlet port to said outlet port when the poppet valve member is in a closed position, said inlet port opening to said intermediate portion of said poppet valve member, means forming a control chamber in said bore open to an opposite end of said poppet valve member from said valve seat and filled with substantially incompressible fluid, sliding seal means between the second end portion of said poppet valve member and surfaces forming said bore to seal said control chamber from said inlet port while permitting said poppet valve member to move to open position, fluid pressure actuated means separate from said first source connected to the inlet port and open to said control chamber to urge said poppet valve member against said valve seat when a desired fluid pressure is present in said control chamber, means having a valve opening to selectively release fluid pressure in said control chamber to permit said poppet valve member to move under pressure present at the inlet port, said poppet valve member moving along said bore to an open position under force generated from fluid pressure at said inlet when it is connected to said first source to permit said inlet port to communicate with the outlet port across said valve seat, accumulator means open only to said control chamber and maintaining the fluid pressure on the substantially incompressible fluid in the control chamber at a desired level, and means forming an orifice substantially larger than the valve opening of the means having a valve opening leading from the control chamber to said accumulator means to control the flow of the substantially incompressible fluid from said control chamber, said orifice thereby controlling the speed of movement of the poppet valve member away from said seat.

5. The combination as specified in claim 4 and threadable adjustable means mounted in said valve body and being threadable toward and away from the end of said poppet valve member opposite from said shoulder means forming said seat to limit the amount that said poppet valve member may move in said bore away from said seat.

6. The control valve of claim 4 in combination with a hydraulic motor comprising a fluid pressure actuator, said actuator having a cylinder body with an interior chamber and a piston slidably mounted in said chamber, an actuator rod extending from said piston to the exterior of said actuator, said piston dividing said chamber into first and second chamber portions, a first chamber portion having an actuator inlet port opening to said outlet port, and means to provide a compressible fluid communicating with said second chamber portion to provide a cushion for movement of said piston tending to reduce the volume of said second chamber portion.

7. The combination of claim 6 wherein said valve body is mounted directly on said actuator and the outlet port and actuator inlet port mate directly with each other.

8. The combination of claim 7 wherein said means to provide a compressible fluid communicating with said second chamber comprises means to fill said second chamber portion with a gaseous fluid.

* * * * *